United States Patent [19]

VandenBerg

[11] Patent Number: Plant 7,468

[45] Date of Patent: Mar. 12, 1991

[54] CHRYSANTHEMUM PLANT NAMED 'ALOUETTE'

[75] Inventor: Cornelis P. VandenBerg, Salinas, Calif.

[73] Assignee: Yoder Brothers, Inc., Barberton, Ohio

[21] Appl. No.: 409,455

[22] Filed: Sep. 18, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Alouette particularly characterized by its flat capitulum form; daisy capitulum type; yellow ray floret color with red-bronze underside of ray florets and red-bronze flower buds; diameter across face of capitulum of 38 to 45 mm at maturity when grown as a pinched spray pot mum; very floriferous with excellent display of many small flowers; uniform seven week photoperiodic flowering response to short days; medium plant height when grown as a pinched pot mum; small, dark green foliage; spreading and very prolific branching pattern; and excellent tolerance to high temperatures for bud initiation and flower development.

3 Drawing Sheets

The present invention comprises a new and distinct cultivar of Chrysanthemum, botanically known as *Dendranthema grandiflora*, and referred to by the cultivar name Alouette.

Alouette, identified as 86-671003, was originated from a cross made by Cornelis P. VandenBerg in a controlled breeding program in Salinas, Calif., in 1986.

The female parent Alouette was an unnamed seedling identified as 83-538021, and described as a white daisy spray pot mum. The male parent of Alouette was an unnamed seedling identified as 83-S01002, and described as a yellow daisy spray pot mum with many very small flowers.

Alouette was discovered and selected as one flowering plant within the progeny of the stated cross by Cornelis P. VandenBerg in January of 1987, in a controlled environment in Salinas, Calif.

The first act of asexual reproduction of Alouette was accomplished when vegetative cuttings were taken from the initial selection in March of 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Alouette are firmly fixed and are retained through successive generations of asexual reproduction.

Alouette has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The high temperature tolerance was determined in a controlled environment in Salinas, Calif., where temperatures were maintained at 35 degrees Celsius during the day and 24 degrees Celsius during the night for the duration of the crop.

The following traits have been repeatedly observed and are determined to be basic characteristics of Alouette, which, in combination, distinguish this Chrysanthemum as a new and distinct cultivar:

1. Flat capitulum form.
2. Daisy capitulum type.
3. Yellow ray floret color, with the underside of the ray florets and the flower buds being red-bronze.
4. Diameter across face of capitulum relatively small, between 38 to 45 mm at maturity, when grown as a pinched spray pot mum.
5. Very floriferous, with excellent display of many small flowers.
6. Uniform seven week photoperiodic flowering response to short days.
7. Medium plant height, requiring 0 to 7 long days after pinch prior to short days and 1 to 2 applications of 2500 ppm B-9 SP to attain a flowered plant height of 25 to 35 cm for year-round flowerings when grown as a pinched pot mum in a 15 cm pot.
8. Small dark green foliage.
9. Branching pattern is spreading and very prolific, each plant having 6 to 8 laterals after pinch.
10. Excellent tolerance to high temperatures for bud initiation and flower development.

The accompanying photographic drawings show typical inflorescence and leaf characteristics of Alouette, with the colors being as nearly true as possible with illustrations of this type.

Sheet 1 is a color photograph of Alouette grown as a pinched spray pot mum grown in a 15 cm pot.

Sheet 2 is a black and white photograph of three views of the inflorescence of Alouette.

Sheet 3 is a black and white photograph showing the upper and under sides of the leaves of Alouette at three stages of development (mature, intermediate and immature).

No commercial cultivar known to the inventor can be compared with Alouette. The combination of yellow flower color with red-bronze underside and buds, very high number of small flowers, small dark green foliage and spreading and very prolific branching pattern is unique, and is not represented in any commercial cultivar known to the inventor.

In the following description, color references are made to the Royal Horticultural Society Colour Chart. The color values were determined on plant material grown as a pinched spray pot mum in Salinas, Calif. on May 31, 1989.

Classification:

*Botanical.*—*Dendranthema grandiflora* cv Alouette.

*Commercial.*—Daisy spray pot mum.

INFLORESCENCE

A. Capitulum:

*Form.*—Flat.

*Type.*—Daisy.

*Diameter across face.*—From 38 to 45 mm at maturity.

B. Corolla of ray florets:

*Color (general tonality from a distance of three meters).*—Yellow, with red-bronze underside and buds.

*Color (upper surface).*—9A to 9B.

*Color (under surface).*—9A, heavily overlaid with 171A to 171B. The midsection of the underside of the ray florets is more heavily overlaid with 171A to 171B than the margins.

*Shape.*—Straight, oblong, slightly ribbed. Apex slightly indented.

C. Corolla of disc florets:

*Color (mature).*—12A.

*Color (immature).*—144B to 144C.

D. Reproductive organs:

*Androecium.*—Present on disc florets only; moderate pollen.

*Gynoecium.*—Present on both ray and disc florets.

PLANT

A. General appearance

*Height.*—Medium; 25 to 35 cm as a pinched spray pot mum with 0 to 7 long days after pinch prior to short days and 1 to 2 applications of 2500 ppm B-9 SP, when grown as a pinched pot mum in a 15 cm pot.

*Branching pattern.*—Spreading and very prolific.

B. Foliage:

*Color (upper surface).*—147A.

*Color (under surface).*—147B.

*Shape.*—Small, lobed and slightly serrated.

I claim:

1. A new and distinct Chrysanthemum plant named Alouette, as described and illustrated.

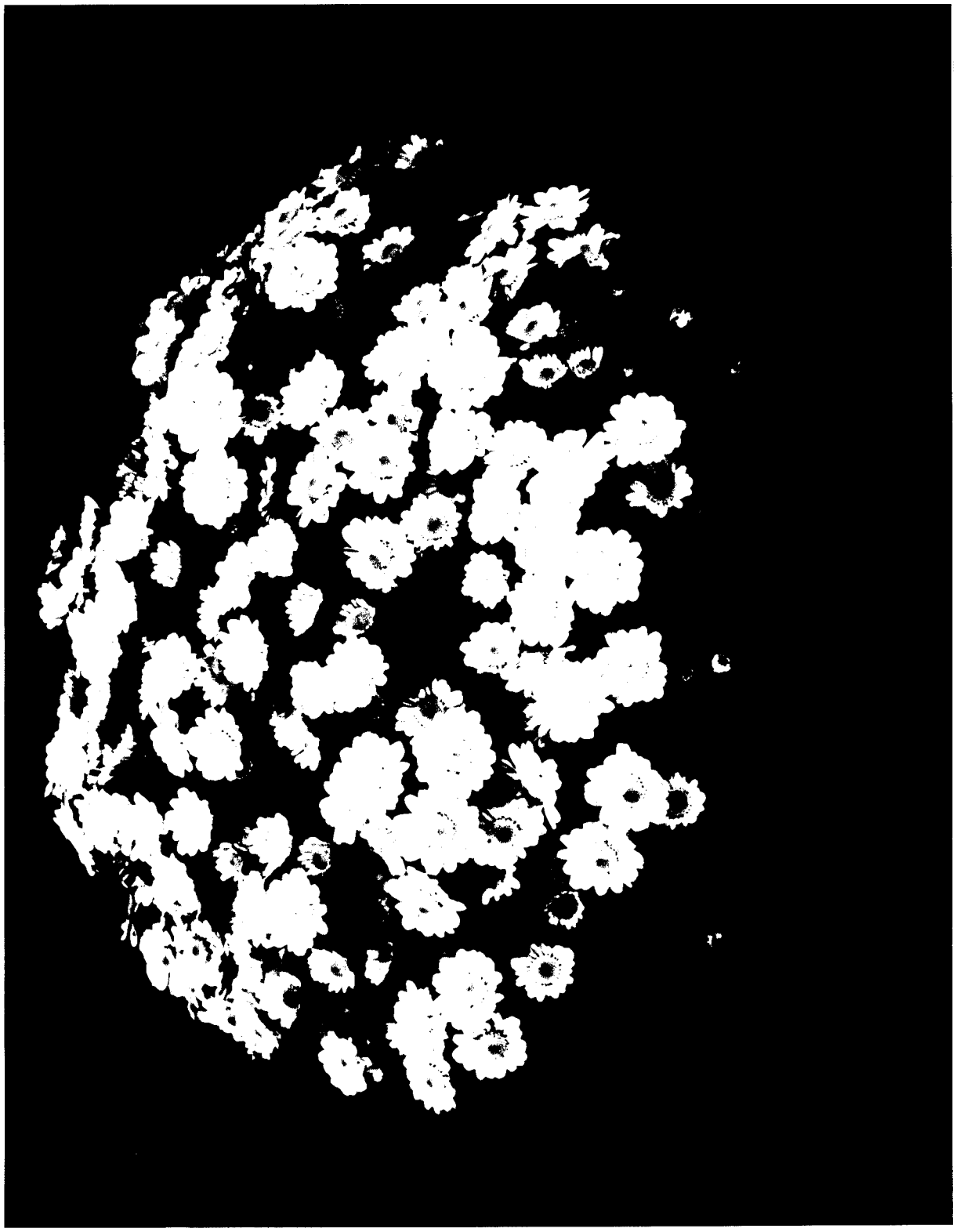

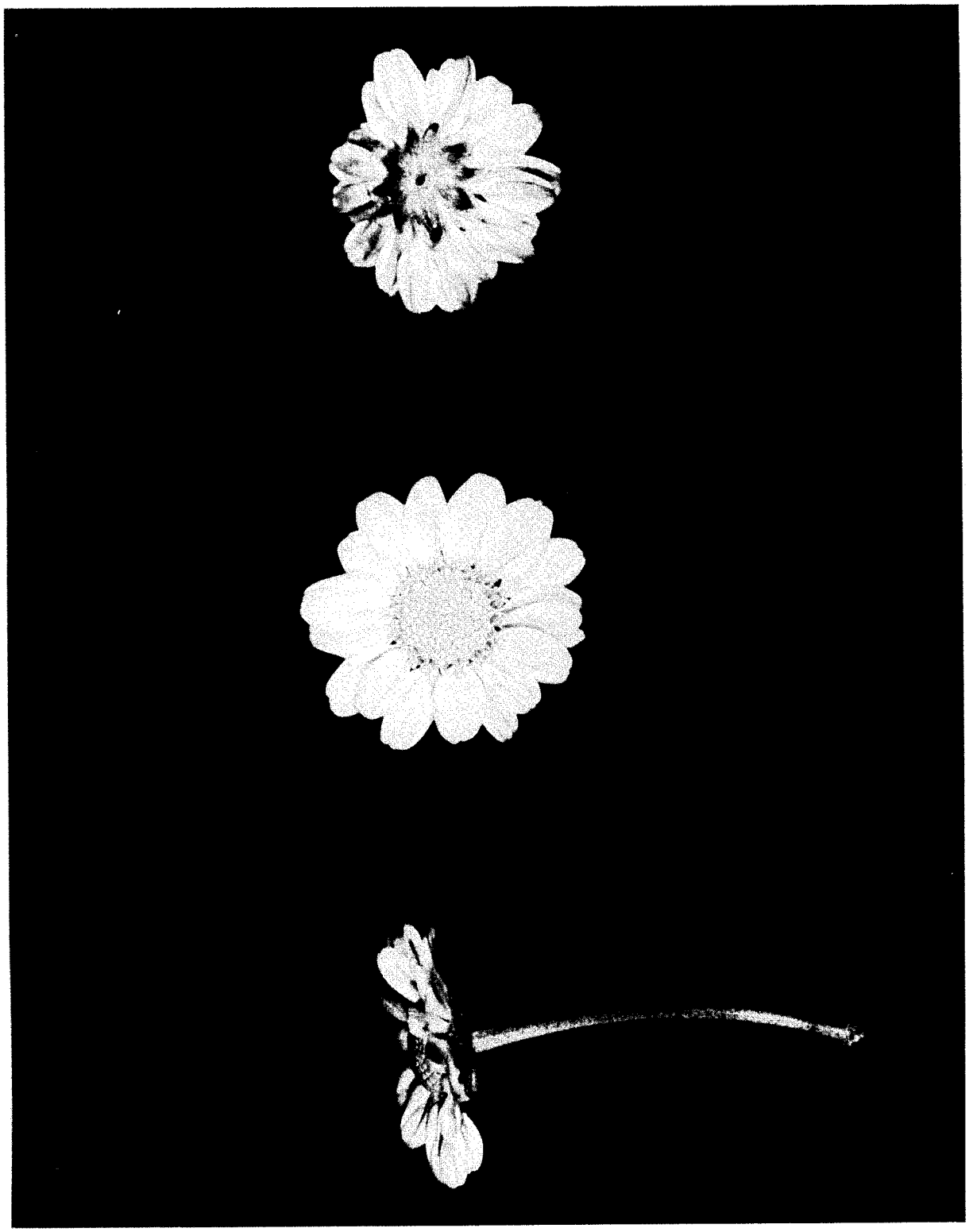

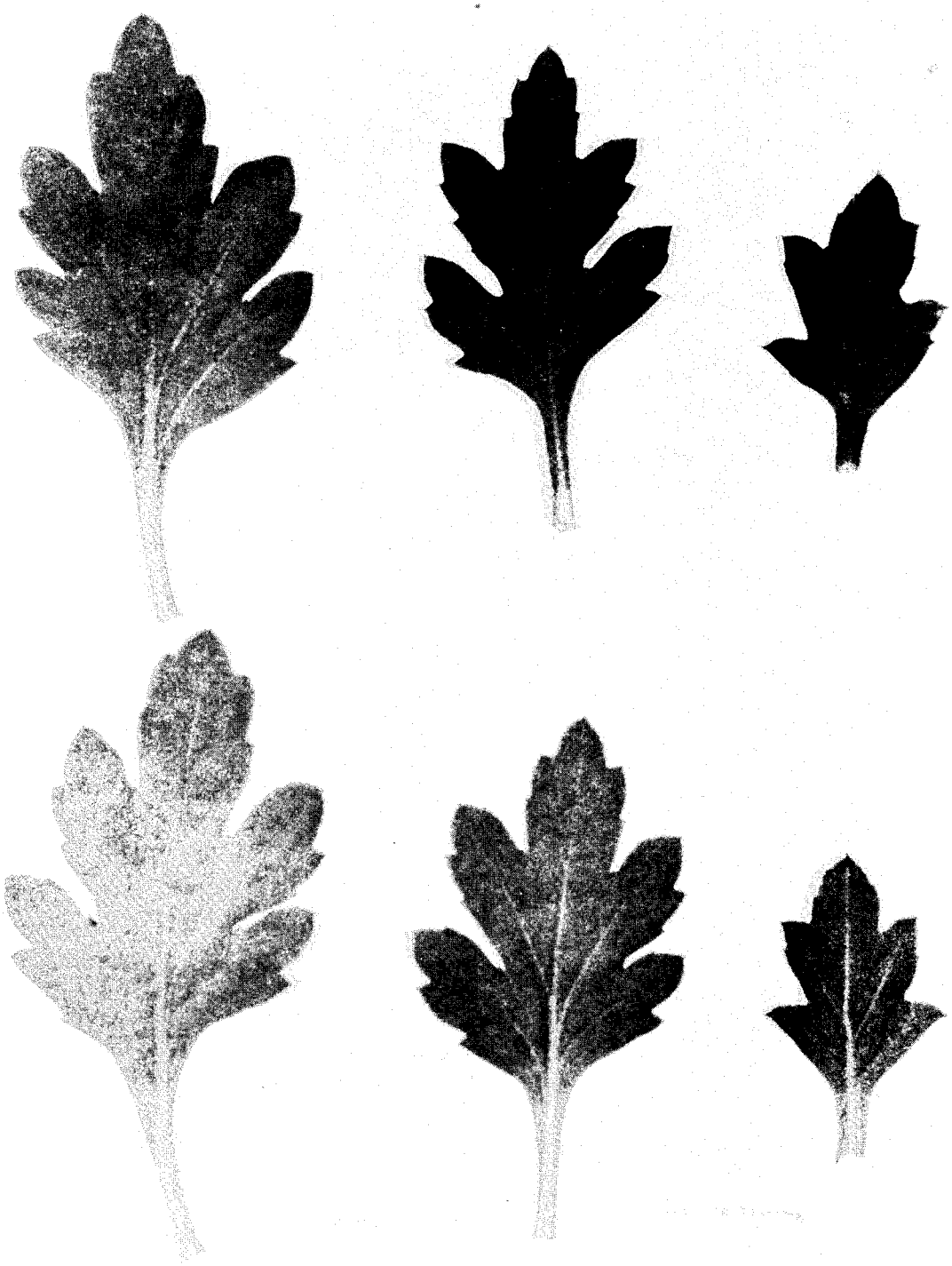

* * * * *